US005591146A

United States Patent [19]

Hasse

[11] Patent Number: 5,591,146
[45] Date of Patent: Jan. 7, 1997

[54] SANITARY NAPKIN WITH PERFUME-BEARING MICROCAPSULE ADHESIVE

[75] Inventor: Margaret H. Hasse, Cincinnati, Ohio

[73] Assignee: The Procter & Gamble Company, Cincinnati, Ohio

[21] Appl. No.: 583,735

[22] Filed: Jan. 17, 1996

[51] Int. Cl.$^6$ .............................. A61F 13/15; A61F 13/20
[52] U.S. Cl. ........................ 604/359; 604/386; 604/390
[58] Field of Search ................................... 604/358, 359, 604/385.1, 386, 387, 389–390

[56] References Cited

U.S. PATENT DOCUMENTS

| | | |
|---|---|---|
| 3,977,992 | 8/1976 | Hofacker . |
| 3,996,156 | 12/1976 | Matsukawa et al. . |
| 4,002,458 | 1/1977 | Hofacker . |
| 4,186,743 | 2/1980 | Steiger ................................ 604/368 |
| 4,409,156 | 10/1983 | Hoshi et al. . |
| 4,460,364 | 7/1984 | Chen et al. . |
| 4,487,801 | 12/1984 | Trunbull et al. . |
| 4,493,869 | 1/1985 | Sweeny et al. . |
| 4,528,226 | 7/1985 | Sweeny . |
| 4,606,956 | 8/1986 | Charbonneau et al. . |
| 4,654,256 | 3/1987 | Doree et al. . |
| 4,661,388 | 4/1987 | Charbonneau . |
| 4,720,417 | 1/1988 | Sweeny et al. . |
| 4,720,423 | 1/1988 | Fraser . |
| 4,769,264 | 9/1988 | Dreger . |
| 4,774,133 | 9/1988 | Doree et al. . |
| 4,847,124 | 7/1989 | Lux Née Andrieux . |
| 4,874,129 | 10/1989 | DiSapio et al. . |
| 4,889,755 | 12/1989 | Charbonneau . |
| 4,961,871 | 10/1990 | Michael . |
| 4,988,557 | 1/1991 | Charbonneau . |
| 5,013,473 | 5/1991 | Norbury et al. . |
| 5,126,061 | 6/1992 | Michael . |
| 5,180,637 | 1/1993 | Sumii . |
| 5,249,676 | 10/1993 | Ashcraft et al. . |
| 5,342,333 | 8/1994 | Tanzer et al. . |
| 5,342,420 | 8/1994 | Bosses . |
| 5,364,380 | 11/1994 | Tanzer et al. . |
| 5,391,420 | 2/1995 | Bootman et al. . |
| 5,395,047 | 3/1995 | Pendergrass, Jr. . |
| 5,489,283 | 2/1996 | Van Tillburg ........................ 604/387 |

*Primary Examiner*—Debra S. Brittingham
*Assistant Examiner*—P. Zuttarelli
*Attorney, Agent, or Firm*—Kevin C. Johnson; Steven W. Miller; Jacobus C. Rasser

[57] ABSTRACT

The present invention relates to a sanitary napkin having an adhesive with perfume carrying release agents. Preferably the release agents are microcapsules that release perfume upon removal of a release liner from the adhesive, and/or during the user's wear of the sanitary napkin, and/or upon the removal of the sanitary napkin from the user's undergarment. The perfume releases are either as fragrance bursts, diffusion or both.

16 Claims, 2 Drawing Sheets

SANITARY NAPKIN WITH PERFUME-BEARING MICROCAPSULE ADHESIVE

FIELD OF THE INVENTION

The present invention relates to sanitary napkins, and more particularly to sanitary napkins including an adhesive layer for securing the sanitary napkin to wearer's undergarment which contains perfume-filled release agents, preferably being microcapsules. The agents release the perfume upon removal of a release liner from the adhesive layer, and/or during the use of the sanitary napkin, and/or upon the removal of the sanitary napkin from a wearer's undergarment.

BACKGROUND OF THE INVENTION

A wide variety of fluid absorbent structures known in the art absorb body fluids such as blood, urine, menses, and the like, and are sanitary and comfortable in use. Disposable products of this type generally comprise a liquid-permeable topsheet, an absorbent core, and a liquid-impermeable backsheet. Various shapes, sizes and thicknesses of such articles have been explored in an attempt to make their use more comfortable and convenient.

Many body fluids have an unpleasant odor, or develop such odors when in contact with air and/or bacteria for prolonged periods. Odor control in sanitary products has been under investigation for many years. Various odor-controlling agents have been disclosed in the literature. For example, U.S. Pat. No. 4,525,410, Hagiwara et al., issued Jun. 25, 1985, discloses zeolite particles (doped with bactericidal cations) held in a fibrous web by incorporating some portion of meltable fibers in the web, and applying heat. These compositions can be used as the outside cover layer in general sanitary goods.

U.S. Pat. No. 2,690,415, F. A. Shuler, issued Sep. 28, 1954, discloses particles of odor-absorbing materials uniformly affixed at the interstices of a permeable web by adhesive to provide an odor absorbent medium; e.g., catamenials. Particulate carbon, silica gel and activated alumina are noted. Shifting/displacement of the particulates is assertedly avoided and the sheet is flexible.

ABSCENTS (odor-control molecular sieve from Union Carbide) for use in diapers and catamenials are specifically noted in Union Carbide brochure (A. J. Gioffre 1988). The brochure indicates that Union Carbide's market research shows potential benefits in such products. U.S. Pat. Nos. 4,795,482 and 4,826,497, relate to ABSCENTS used as an odor-controlling agent, generally, and in sanitary products, in particular.

Activated carbon is a very effective odor absorber, with average internal surface area of about 1000 $m^2/g$. However, activated carbon is not readily incorporated into consumer products.

Zeolites have smaller surface area, in the range of about 400–800 $m^2/g$. However, zeolites may absorb the moisture in body fluids (i.e., water) over other fluids, which may compromise its effectiveness. Furthermore, activated carbon and zeolites have open structures, and continuously absorb airborne organic vapor, unless hermetically sealed. Therefore, during storage, these odor adsorbents can become saturated and less efficient before the products are used.

Consumers desire not to be exposed to body malodor and to feel "fresh" during the course of the wear of a sanitary napkin. Thus, the present invention provides fragrance bursts of perfume either prior to the placement of the sanitary napkin, use of the sanitary napkin, and/or at its removal from a wearer's undergarments. In addition, a pleasant fragrance may be sustained by the use of microcapsules which diffuse perfume during wear of the sanitary napkin.

SUMMARY OF THE INVENTION

Accordingly, the present invention provides a sanitary napkin for placement in a wearer's undergarment which has a longitudinal axis, a lateral axis, longitudinal edges, end edges, and a central portion. The sanitary napkin comprises a liquid pervious topsheet and a liquid impervious backsheet joined to the topsheet. The backsheet has an outer surface and an inner surface. An absorbent core is positioned between the topsheet and the backsheet. An attachment system is secured to the outer surface of the backsheet to attach the sanitary napkin to a wearer's undergarment. A plurality of perfume-filled release agents are at least partially embedded within the attachment system. In a preferred embodiment the release agents comprise microcapsules. The attachment system preferably comprises an adhesive layer having a release liner thereon to protect the adhesive layer prior to engagement of the sanitary napkin to a wearer's undergarment and to facilitate release of perfume from the perfume-filled microcapsules.

In one embodiment of the present invention, the adhesive layer comprises perfume-filled microcapsules that provide a fragrance burst upon removal of the release liner from the adhesive layer. In another embodiment, the adhesive layer comprises perfume-filled microcapsules that diffusely release perfume at a steady-state throughout the engagement of the sanitary napkin with a user's undergarment. Yet another embodiment provides an adhesive layer that comprises perfume-filled microcapsules which provide a fragrance burst upon disengagement of the sanitary napkin from a wearer's undergarments. Another embodiment exists wherein a fragrance burst and steady-state diffusion of perfume from perfume-filled microcapsules occurs at the removal of the release liner for engagement of the sanitary napkin with a wearer's undergarment, during wear of the sanitary napkin, and at disengagement of the sanitary napkin from a wearer's undergarment.

Alternatively, the sanitary napkin may comprise a pair of flaps which have an attachment system for attachment of the sanitary napkin to an undergarment. The flaps have a garment side on which rests the attachment system and each flap is associated with the sanitary napkin's central portion at a juncture and extends laterally outward beyond a longitudinal edge of the central portion. Each juncture has a pair of ends. Each flap is divided into a front half and a back half by a flap transverse centerline. Preferably, the attachment system on the flaps comprises an adhesive layer having a release liner thereon to protect it prior to engagement of the sanitary napkin to a wearer's undergarment. Preferably, the adhesive layer on the flaps comprises perfume-filled microcapsules which provide a fragrance burst upon removal of the release liner from the adhesive layer, steady-state diffusion of perfume throughout the wear of the sanitary napkin at the removal of the release liner from the adhesive layer, and/or a fragrance burst upon disengagement of the sanitary napkin from a wearer's undergarment.

An alternative embodiment herein is an attachment system which comprises perfume-filled microcapsules residing only on the flaps as previously indicated. Another alternative attachment system herein is one comprising hooks and loops or other mechanical means with a plurality of release agents residing therein.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad. A preferred embodiment of a unitary disposable absorbent article of the present invention is the catamenial pad, sanitary napkin 20, shown in FIG. 1. As used herein, the term "sanitary napkin" or "napkin" refers to devices which absorb and contain body exudates, and more specifically, refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. The term "perfume" as used herein refers to odor absorbing and/or masking agents such as volatile perfumes, essences, fragrances, zeolites, activated carbon, cyclodextrins, mixtures thereof and the like. The term "release agent" as used herein refers to any suitable means known in the art for the containment and release of perfume as described herein. The term "microcapsules" or "microspheres" as used herein refers to a release agent and/or containment assembly for holding and later distributing perfume. The term "embedded" as used herein refers to the integration of one material within and/or on another material, e.g., microcapsules embedded on a substrate. The term "perfume-filled" as used herein refers to microcapsules that are at least partially filled with perfume as defined herein. The term "fragrance burst" as used herein refers to the immediate release of perfume resulting from bursting perfume-filled microcapsules which contain perfume. The term "steady-state" as used herein refers to a substantially continuous release of perfume from a perfume-filled release agent. It should be understood, however, that the present invention is also applicable to other absorbent articles such as incontinence briefs, training pants, other feminine hygiene garments, disposable diapers and the like.

Figure 1:
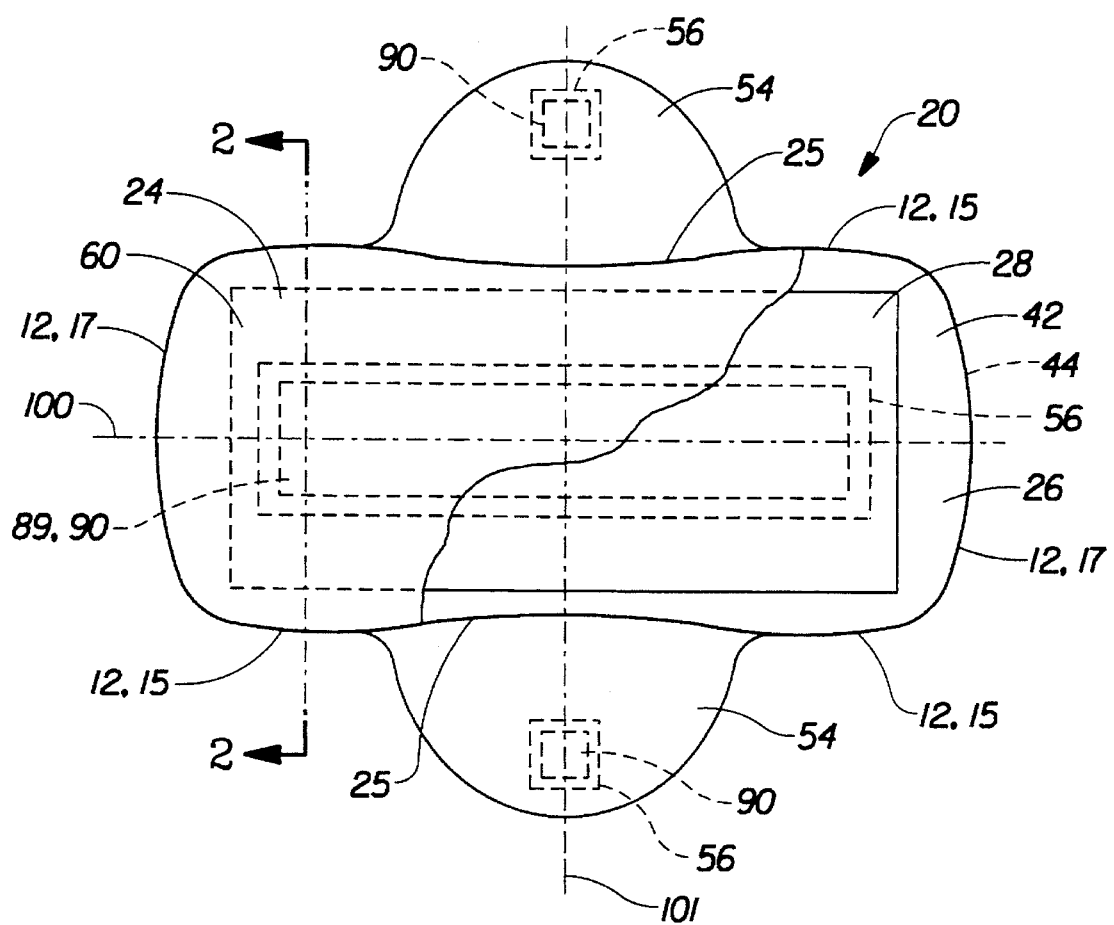
FIG. 1 is a plan view of the sanitary napkin embodiment of the present invention having portions cut-away to reveal underlying structure, the wearer contacting surface of the sanitary napkin facing the viewer.

FIG. 1 is a plan view of the sanitary napkin 20 of the present invention in its flat-out state with portions of the structure being cut-away to more clearly show the construction of the sanitary napkin 20 and with the portion of the sanitary napkin 20 which faces or contacts the wearer, oriented towards the viewer. As shown in FIG. 1, the sanitary napkin 20 preferably comprises a liquid pervious topsheet 24, a liquid impervious backsheet 26 joined with the topsheet 24, an absorbent core 28 positioned between the topsheet 24 and the backsheet 26, and adhesive-embedded microcapsules (not shown in FIG. 1).

The sanitary napkin 20 has two surfaces, a body-contacting surface 60 or "body surface" and a garment surface 65. The sanitary napkin 20 is shown in FIG. 1 as viewed from its body surface. The body surface 60 is intended to be worn adjacent to the body of the wearer while the garment surface 65 is on the opposite side and is intended to be placed adjacent to the wearer's undergarments when the sanitary napkin 20 is worn. The sanitary napkin 20 has two centerlines, a longitudinal centerline 100 and a transverse centerline 101. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction. FIG. 1 also shows that the sanitary napkin 20 has a periphery 12 which is defined by the outer edges of the sanitary napkin 20 in which the longitudinal edges are designated 15 and the end edges are designated 17.

While the topsheet, the backsheet, and the absorbent core may be assembled in a variety of well known configurations (including so called "tube" products or side flap products), preferred sanitary napkin configurations are described generally in U.S. Pat. No. 4,950,264, "Thin, Flexible Sanitary Napkin" issued to Osborn on Aug. 21, 1990; U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; U.S. Pat. No. 4,589,876, "Shaped Sanitary Napkin With Flaps" issued to Van Tilburg on Aug. 18, 1987. Each of these patents are hereby incorporated herein by reference. FIG. 1 shows a preferred embodiment of the sanitary napkin 20 in which the topsheet 24 and the backsheet 26 have length and width dimensions generally larger than those of the absorbent core 28. The topsheet 24 and the backsheet 26 extend beyond the edges of the absorbent core 28 to thereby form not only portions of the periphery but also side flaps 54.

The absorbent core 28 may be any absorbent means which is capable of absorbing or retaining liquids (e.g., menses and/or urine). As shown in FIG. 1, the absorbent core 28 has a body surface, a garment surface, side edges, and pad edges. The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams: absorbent sponges; superabsorbent polymers; absorbent gelling materials; or any equivalent material or combinations of materials, or mixtures of these. The configuration and construction of the absorbent core 28 may also be varied (e.g., the absorbent core 28 may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 28 should, however, be compatible with the design loading and the intended use of the sanitary napkin 20. Further, the size and absorbent capacity of the absorbent core 28 may be varied to accommodate different uses such as incontinence pads, pantiliners, regular sanitary napkins, or overnight sanitary napkins.

Exemplary absorbent structures for use as the absorbent core 28 of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The backsheet 26 and the topsheet 24 are positioned adjacent the garment surface and the body surface, respectively, of the absorbent core 28 and are preferably joined thereto and to each other by attachment means (not shown) such as those well known in the art. For example, the backsheet 26 and/or the topsheet 24 may be secured to the absorbent core 28 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 26 has an inner surface 42 and an outer surface 44 opposed to the inner surface 42. The backsheet 26 prevents the exudates absorbed and contained in the absorbent core 28 from wetting articles which contact the sanitary napkin 20 such as pants, pajamas and undergarments. The backsheet 26 may thus comprise a woven or nonwoven material, polymeric films such as thermoplastic films of polyethylene or polypropylene, or composite materials such as a film-coated nonwoven material. Preferably, the backsheet 26 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P 18-0401 and by Tredegar, Incorporated, of Terre Haute, Ind., under the designation XP-39385. The backsheet 26 is preferably embossed and/or matte finished to provide a more clothlike appearance. Further, the backsheet 26 may permit vapors to escape from the absorbent core 28 (i.e., breathable) while still preventing exudates from passing through the backsheet 26.

The topsheet 24 is compliant, soft feeling, and non-irritating to the wearer's skin. Further, the topsheet 24 is liquid pervious permitting liquids (e.g., menses and/or urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et at. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated herein by reference. Alternatively, the body surface of the topsheet can be made hydrophilic by treating it with a surfactant such as is described in the above referenced U.S. Pat. No. 4,950,254 issued to Osborn, incorporated herein by reference.

In use, the sanitary napkin 20 is held in place in a wearer's undergarment by an attachment system 89 secured to the outer surface 44 of the backsheet 26. The attachment system 89 may comprise any support means or attachment means well-known for such purposes. A suitable attachment system 89 is adhesive layer 90, sometimes called panty fastening adhesive. The adhesive layer 90 provides a means for securing the sanitary napkin 20 in the crotch portion of the panty. Thus, a portion of or all of the outer surface 44 of the backsheet 26 is coated with adhesive layer 90. Any adhesive or glue used in the art for such purposes can be used for the adhesive 90 herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the sanitary napkin 20 is placed in use, the pressure-sensitive adhesive layer 90 is typically covered with a removable release liner 56 in order to keep the adhesive layer from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. In a preferred embodiment, the sanitary napkin 20 of the present invention is used by removing the release liner 56, and thereafter placing the sanitary napkin 20 in a panty so that the adhesive layer 90 contacts the panty. As one function, the adhesive layer 90 maintains the sanitary napkin 20 in its position within the panty during use.

In a preferred embodiment of the present invention, FIG. 1 shows the sanitary napkin having two flaps 54 each of which are adjacent to and extend laterally from the side edges of the absorbent core. The flaps 54 are configured to drape over the edges of the wearer's panties in the crotch region so that the flaps 54 are disposed between the edges of the wearer's panties and the thighs. The flaps 54 serve at least three purposes. First, the flaps help serve to prevent soiling of the wearer's body and panties by menstrual fluid, preferably by forming a double wall barrier along the edges of the panty. Second, the flaps 54 are preferably provided with attachment means on their garment surface so that the flaps 54 can fold back under the panty and attach to the garment facing side of the panty or one flap 54 to another. In this way, the flaps 54 serve to keep the sanitary napkin 20 properly positioned in the panty. Third and preferably, the flaps 54 can contain perfume microcapsules which release perfume as a fragrance burst at the placement or disengagement of the sanitary napkin 20 in a wearer's undergarment and/or release perfume as a result of forces which may be generated by a wearer's movement, thereby causing releases of perfume continuously throughout the wear of the napkin 20. The flaps 54 can be constructed of various materials including materials similar to the topsheet 24, backsheet 26, tissue, or combination of these materials. Further, the flaps 54 may be a separate element attached to the main body of the napkin 20 or can comprise extensions of the topsheet 24 and backsheet 26 (i.e., a unitary construction). A number of sanitary napkins having flaps suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; U.S. Pat. No. 4,589,876 entitled "Sanitary Napkin", which issued to Van Tilburg on May 20, 1986; and U.S. Pat. No. 4,608,047, entitled "Sanitary Napkin Attachment Means", which issued to Mattingly on Aug. 26, 1986. Each of these patents are incorporated herein by reference.

Figure 2:
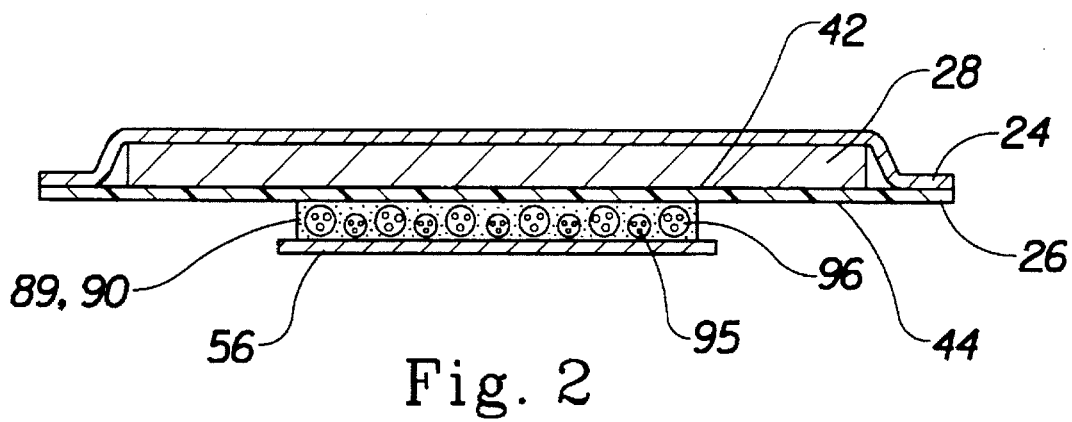
FIG. 2 is a cross-sectional view of the sanitary napkin taken along line 2—2 of FIG. 1, showing the microcapsules embedded within the adhesive.

FIG. 2 shows fragrance burst microcapsules 96 and diffusion microcapsules 95 embedded within adhesive layer 90. Adhesive layer 90 is covered by the release liner 56. FIG. 2 demonstrates a side-by-side arrangement of two microcapsule types, but it would be obvious to any one skilled in the art that any physical arrangement of the microcapsules that produces the desired fragrance burst and/or diffusion perfume release may be utilized. Also, more than two types of microcapsules could be used to produce the desired result.

As used herein, the term "cyclodextrin" includes any of the known cyclodextrins such as unsubstituted cyclodextrins containing from six to twelve glucose units, especially, alpha-, beta-, and gamma-cyclodextrins, and/or their derivatives, and/or mixtures thereof. The alpha-cyclodextrin consists of 6, the beta-cyclodextrin 7, and the gamma-cyclodextrin 8, glucose units arranged in a donut-shaped ring. The specific coupling and conformation of the glucose units give the cyclodextrins a rigid, conical molecular structure with a hollow interior of a specific is volume. The "lining" of the internal cavity is formed by hydrogen atoms and glycosidic bridging oxygen atoms, therefore this surface is fairly hydrophobic. These cavities can be filled with all or a portion of an organic molecule with suitable size to form an "inclusion complex." Alpha-, beta-, and gamma-cyclodextrins can be obtained from, among others, American Maize-Products Company (Amaizo), Hammond, Ind.

Cyclodextrin derivatives are disclosed in U.S. Pat. Nos: 3,426,011, Parmerter et al., issued Feb. 4, 1969; 3,453,257, 3,453,258, 3,453,259, and 3,453,260, all in the names of Parmerter et al., and all also issued Jul. 1, 1969; 3,459,731, Gramera et al., issued Aug. 5, 1969; 3,553,191, Parmerter et al., issued Jan. 5, 1971; 3,565,887, Parmerter et al., issued Feb. 23, 1971; 4,535,152, Szejtli et al., issued Aug. 13, 1985; 4,616,008, Hirai et al., issued Oct. 7, 1986; 4,638,058, Brandt et al., issued Jan. 20, 1987; 4,746,734, Tsuchiyama et al., issued May 24, 1988; and 4,678,598, Ogino et al., issued Jul. 7, 1987, all of said patents being incorporated herein by reference. Examples of cyclodextrin derivatives suitable for use herein are methyl-betacyclodextrin, hydroxyethyl-beta-cyclodextrin, and hydroxypropyl-beta-cyclodextrin of different degrees of substitution (D.S.), available from Amaizo; Wacker Chemicals (USA), Inc.; and Aldrich Chemical Company. Water-soluble derivatives are also highly desirable.

The compositions and articles of this invention optionally contain, in addition to uncomplexed, small particle size cyclodextrins, an effective, i.e., odor-controlling, amount of various additional adjunct odor-controlling materials. Incorporating adjunct odor-controlling materials will enhance cyclodextrin's capacity for controlling odors, as well as the range of odor types being controlled. Such materials include, for example, zeolites, activated carbon, kieselguhr, and water-soluble antibacterial compounds, such as cetyl pyridinium chloride, zinc chloride, copper salts, copper ions, chlorhexidine, quaternary ammonium compounds, chelating agents, parabens, chitin, pH buffered materials, and the like. Especially preferred is zeolite material having "intermediate" silicate/aluminate ratios.

A wide variety of intermediate zeolites suitable for use herein are commercially available as VALFOR CP301-68, VALFOR 300-63, VALFOR CP300-35 and VALFOR CP300-56, from PQ Corporation, and the CBV100 series (other than Mordenite, as noted below) of zeolites from Conteka.

In the event the zeolites herein are optionally to be used in conjunction with the activated carbon, it is preferred (for aesthetics reasons) to coat the carbon with the zeolite using a binder.

Other odor-controlling agents include kieselguhr, and water-soluble antibacterial compounds, such as cetyl pyridinium chloride, zinc chloride, copper salts, copper ions, chlorhexidine, quaternary ammonium compounds, chelating agents, parabens, chitin, pH buffered materials, and the like.

The perfume ingredients and compositions of this invention are the conventional ones known in the art. Selection of any perfume component, or amount of perfume, is based on functional and aesthetic considerations. Preferred perfume components useful in the present invention are the highly volatile, and the moderately volatile perfume ingredients, more preferably the highly volatile, low boiling ingredients.

The highly volatile, low boiling, perfume ingredients typically have boiling points of about 250° C. or lower. These highly volatile perfume ingredients are fleeting and are quickly lost as they are released. Many of the more moderately volatile perfume ingredients are also quickly lost. The moderately volatile perfume ingredients are those having boiling points of from about 250° C. to about 300° C. Many of the perfume ingredients as discussed hereinafter, along with their odor characters, and their physical and chemical properties, such as boiling point and molecular weight, are given in "Perfume and Flavor Chemicals (Aroma Chemicals)," Steffen Arctander, published by the author, 1969, incorporated herein by reference.

Examples of the highly volatile, low boiling, perfume ingredients are: anethole, benzaldehyde, benzyl acetate, benzyl alcohol, benzyl formate, iso-bornyl acetate, camphene, cis-citral (neral), citronellal, citronellol, citronellyl acetate, para-cymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, alpha-pinene, beta-pinene, gamma-terpinene, alpha-terpineol, beta-terpineol, terpinyl acetate, and vertenex (para-tertiary-butyl cyclohexyl acetate). Some natural oils also contain large percentages of highly volatile perfume ingredients. For example, lavandin contains as major components: linalool; linalyl acetate; geraniol; and citronellol. Lemon oil and orange terpenes both contain about 95% of d-limonene.

Examples of moderately volatile perfume ingredients are: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para-tertiarybutyl-alpha-methyl hydrocinnamic aldehyde), gamma-metyhyl ionone, nerolidol, patchouli alcohol, phenyl hexanol, beta-selinene, trichloromethyl phenyl carbinyl acetate, triethyl citrate, vanillin, and veratraldehyde. Cedarwood terpenes are composed mainly of alpha-cedrene, beta-cedrene, and other $C_{15}H_{24}$ sesquiterpenes.

The perfume/cyclodextrin inclusion complexes of this invention are formed in any of the ways known in the art. Typically, the complexes are formed either by bringing the perfume and the cyclodextrin together in a suitable solvent, e.g., water, or, preferably, by kneading/slurrying the ingredients together in the presence of a suitable, preferably minimal, amount of solvent, preferably water. The kneading/slurrying method is particularly desirable because it results in smaller particles so that there is less, or no, need to reduce the particle size. In addition, less solvent is needed and therefore less separation of the solvent is required. Disclosures of complex formation can be found in Atwood, J. L., J. E. D. Davies & D. D. MacNichol, (Ed.): *Inclusion Compounds*, Vol. III, Academic Press (1984), especially Chapter 11, Atwood, J. L. and J. E. D. Davies (Ed.): *Proceedings of the Second International Symposium of Cyclodextrins* Tokyo, Japan, (July, 1984), and J. Szejtli, *Cyclodextrin Technology*, Kluwer Academic Publishers (1988). These publications are incorporated herein by reference.

Figure 3:
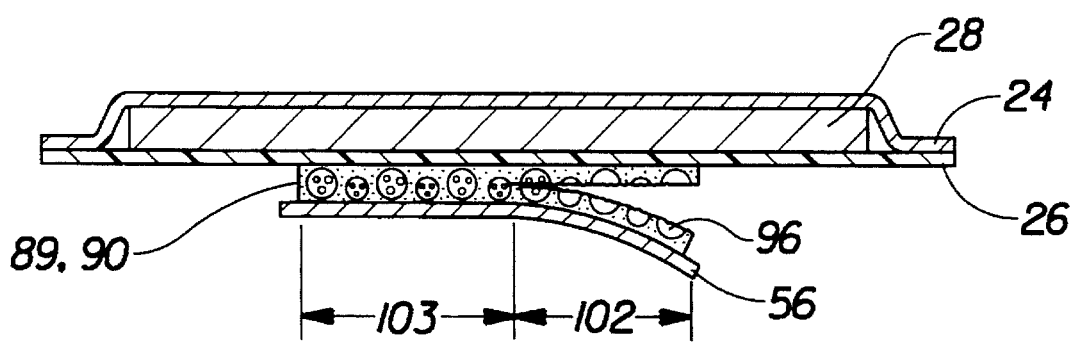
FIG. 3 is a cross-sectional view of the microcapsules at disengagement of the liner from the adhesive.

FIG. 3 illustrates schematically one mechanism believed to be the operative one in insuring that a controlled amount of perfume is released from the microcapsules 96 just prior to use, i.e., the fragrance burst microcapsules. Referring to the unpeeled portion 103 of the release liner 56, it can be seen that a portion of at least some of the microcapsules 96 are embedded and gripped by a layer of adhesive layer 90 prior to removal of the release liner 56. Referring now to the separated portion 102 of the release liner 56, it can be seen that the act of separating, which produces a shear force across the microcapsules 96, facilitates their rupture, thus releasing the perfume contained in the microcapsules. Because the forces applied and the manner in which the release liner 56 is peeled from the adhesive layer 90 almost invariably is constant from user to user and from time to time, those factors which control the number of microcapsules 96 ruptured and hence the quantity of perfume released are substantially entirely within the control of the manufacturer. Such factors are the rupture strength of the microcapsules 96, the number and distribution of the microcapsules 96, the quantity of perfume in each microcapsule 96 and the relative adhesion of the microcapsules 96 to the adhesive layer 90 as compared to the rupture strength of the microcapsules 96. With respect to the latter factor, it is clear that both the force required to separate the microcapsules 96 from the adhesive layer 90 should be greater than the force required to rupture the microcapsules 96. If this condition is met, microcapsules 96 embedded within the adhesive layer 90 will rupture.

At placement of the sanitary napkin 20 in a wearer's undergarment, the release liners 56 on the backsheet 26 and on the flaps 54 which protect the adhesive layer 90 are removed from the adhesive-containing backsheet 26 and flaps 54. The adhesives 90 herein can contain one type of microcapsule performing various functions and/or as shown in FIG. 3, can contain at least two types of microcapsules performing differing functions. For example, microcapsule 96 provides a fragrance burst at the removal of the release liner 56 and/or a fragrance burst at the disengagement of the sanitary napkin 20 from the user's undergarment. Microcapsule 95 diffusely releases perfume at the removal of the release liners 56 from the adhesive layer 90 on the flaps 54 and backsheet 26. These various functions can be combined into one type of microcapsule or perfume release agent.

Therefore, at the initial introduction of the sanitary napkin 20 to the wearer's undergarment, a fragrance burst, i.e., the release of perfume resulting from bursting microcapsules 96 can occur. Also, at exposure to the air by the removal of the release liners 56 and 57, other perfume-diffuse microcapsules 95 can begin diffusing perfume. Next, at disengagement of the sanitary napkin 20 from a wearer's undergarment, another fragrance burst can occur either from the same type of microcapsule 96 used in the first fragrance burst or from compatible alternatives. Alternatively, microcapsules may be designed to burst during wear of the article as a result of frictional forces caused by pressure and movement placed on the pad during body movement. Pressures from walking and sitting are normally in the range of 0.25 to 0.8 psi. Changes in body position (e.g., crossing the legs) can exert several times normal pressure on the pad, which can burst capsules. While not wishing to be bound by any particular theory, it is believed that movement of the body against the pad can cause the pad to be displaced resulting in a shearing of capsules. Finally, note that at removal and disposal of the sanitary napkin 20, perfume can preferably continue to diffuse while in a disposal receptacle to mask malodor from body exudates.

It is also desirable to have the construction resist the effects of variable ambient conditions. It is therefore desirable that rupture strength exceed 4.0 g/cm (as measured by an Instron force gauge measuring device made commercially available by the Instron Corporation of Canton, Mass.) after storage at 120° C., and less than 1% R.H. for seventy-two hours. This test would be performed by storage in an oven, removal to a neutral environment (e.g., sealed bag or jar) until the article is at room temperature, and then measuring the rupture strength. It is preferred that the rupture strength is at least 8.0 g/cm and most preferred that the rupture strength is at least 16 g/cm under those conditions. The article must still display a rupture strength between 2 and 90 g/cm at 20° and 50% R.H. Using microcapsules which are greater than 30 microns and up to 50 microns in size, and that do not degrade as a result of contact with moisture. As such, these microcapsules will provide a useful microcapsule-containing adhesive layer 90.

Microcapsules for use in this invention can be made by any of several well-known encapsulating processes. Examples of appropriate processes include chemical encapsulating processes and mechanical encapsulating processes. A wide variety of processes exist by which microcapsules can be manufactured. These varied processes provide different techniques for producing microcapsules of varying sizes, alternative materials for the composition of the capsule shell and various different functional materials within the shell. Some of these various processes are shown in U.S. Pat. Nos. 3,516,846; 3,516,941; 3,996,156; 4,409,156 and 5,180,637 and British patent specification Nos. 1,156,725; 2,041,319 and 2,048,206, and each is incorporated herein by reference.

An example of a mechanical encapsulating process is the impingement of droplets of the material to be encapsulated (i.e., in the case of this invention, a perfume or other deodorant composition) upon liquid or semi-solid films of intended capsule wall material; separation of the thereby encapsulated droplet from the film of impingement; and solidification of the microcapsule wall material.

Chemical encapsulating processes generally include combining a first reactive material in a continuous phase capsule manufacturing vehicle and a second reactive material into droplets to be encapsulated. The droplets are then dispersed in the manufacturing vehicle and a reaction between the reactive materials is effected. Liquid-liquid phase separation of the polymeric capsule wall material from the vehicle is carded out wherein the phase-separated polymeric material wets and enwraps the dispersed droplets to be encapsulated.

A wide variety of different materials may also be used in making the capsule shells. A popular material for shell formation is the polymerization reaction product between urea and formaldehyde or melamine and formaldehyde, or the polycondensation products of monomeric or low molecular weight polymers of dimethylolurea or methylolated urea with aldehydes. A variety of capsule forming materials are disclosed, for example, in U.S. Pat. Nos. 3,516,846 and 4,087,376 and British patent specification Nos. 2,006,709 and 2,062,570, and each is incorporated herein by reference.

The adhesive layer for the microcapsules should form a bond to the wearer's undergarment which is stronger than the cohesive strength of the adhesive with the microcapsules dispersed therein. Although it is generally desirable to have an adhesive, the absolute cohesive strength of which is less than its adhesive strength to the surface of the wearer's undergarment, this is not essential. When microcapsules are included within the adhesive layer, the effective cohesive strength of the adhesive tends to be reduced.

It has also been found that microcapsule size plays a role in the usefulness of microcapsules according to the practice of the present invention. Generally the microcapsules should have an average diameter between 5 and 100 microns and preferably between 12 and 30 microns when the capsule payload is between 80 and 90% by weight of the total capsule weight. It is highly preferred that the microcapsules have an average diameter between 14 and 60 microns and it is most preferred that the microcapsules have a diameter between 15 and 25 microns. These dimensions play a surprisingly important role in the ability to control the percentage of rupture of microcapsules in the practice of the present invention. With lower payloads (e.g., 70–80%), the microcapsules should be larger to provide the necessary rupture strength. The broadest range of average capsule size under most conditions would be about 5 to 100 microns. When 8 micron microcapsules are used, a 90–95% by weight payload is preferred. Generally preferred are microcapsules having sizes of between 8 and 30 micrometers.

The microcapsules can form between 20 and 99 percent by volume of the total adhesive composition, but most preferably between 30 and 75 percent of this total composition volume. The absolute peel force tends to be dependent on the weight of the base coat and relatively independent of the amount of microcapsules (up to 50% by weight of microcapsules per unit area).

The microcapsule-beating adhesive layer is coated onto a portion of the adhesive surface which is located within a backsheet and/or flap attachment system. Preferably, this adhesive is the sole bonding material between the sanitary napkin and the wearer's undergarment. Alternatively, two adhesives may be used in which one secures the microcapsules to the backsheet and the other adhesive is used to secure the sanitary napkin to the wearer's undergarment. If any effective amount of adhesive is present in the areas where microcapsules are deposited and they are not ruptured by separation of the sanitary napkin from the wearer's undergarment, it is then preferable that the cohesive strength of that adhesive be lower than the rupture strength of the microcapsules, e.g., this could occur in an alternative embodiment that primarily uses diffusion microcapsules that will not be ruptured.

The nature and composition of the adhesive is not critical to the practice of the invention as long as the adhesive is capable of adherently bonding the microcapsules to the outer surface of the backsheet, and also, the adhesive layer must be readily removable from a wearer's undergarment. The quantity of adhesive layer must be sufficient to hold the microcapsules in place on the surface of the wearer's undergarment until rupture of the microcapsules at removal of the sanitary napkin from the wearer. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697.

Preferably, the adhesive is an acrylate- or methacrylate-based adhesive system comprising infusible, solvent dispersible, solvent insoluble, inherently tacky, elastomeric copolymer microspheres as disclosed in U.S. Pat. No. 3,691,140. Alternatively, this adhesive composition may comprise hollow, polymer, acrylate, infusible, inherently tacky, solvent insoluble, solvent dispersible, elastomeric pressure-sensitive adhesive microspheres as disclosed in U.S. Pat. No. 5,045,569. Washing of the microcapsules before mixing them with the adhesive layer often tends to provide more consistency in their properties by removing low molecular weight, unreacted materials.

Capsule wall materials suitable for use in accordance with the teachings of this invention include any appropriate polymeric film-forming material. For example, microcapsules 96 may be made from natural hydrophilic polymeric materials such as gelatin, gum arabic, starch, carrageenin, and zein; natural polymeric materials modified in some way such as ethyl cellulose, carboxymethyl cellulose, shellac, resin and nitrocellulose; and other polymeric materials such as polyvinyl alcohol, polyethylene, polystyrene, polyacrylamide, polyether, polyester, polybutadiene, silicone, epoxy and polyurethane.

The particular perfume or encapsulated deodorant forms no part of this invention and may be varied to so great a degree as to defy classification or description. Reference is made, instead, to "Cosmetics, Science and Technology," second edition, edited by M. S. Balsam and Edward Sagatin and published by John Wiley & Sons, Inc., of New York, 1972. In particular, reference is made to Chapter 32, "Fragrance" written by M. S. Balsam for examples of the variety of perfume formulations possible.

The material contained in the microcapsules can be any of a variety of liquids, including solutions, dispersions, and gelled materials. Preferred types of ingredients are organic solids which are fragrance-releasing materials that readily volatilize upon rupturing of the microcapsules. The most preferred types of ingredients would be fragrant materials (such as essences and most preferably medium to highly volatile perfumes) or materials which provide chemically active vapors or liquids (e.g., bacteriostats or deodorants). Whatever the fragrance, it or they should be chosen to be compatible with typical undergarment materials and all other sanitary napkin components.

The use of diffusion microcapsules which provide varying rates of diffusion are contemplated. For example, microcapsules may diffuse at any of the rates of the following:

i) at steady-state or zero-order release rate in which there is a substantially continuous release per unit of time;

ii) a first-order release rate in which the rate of release declines towards zero with time; and iii) a delayed release in which the initial rate is slow, but then increases with time.

An alternative embodiment is also contemplated wherein the sanitary napkin 20 has no flaps 54. Thus, microcapsule-bearing adhesive layer 90 will primarily exist only on the backsheet 26 and can contain any of the microcapsule configurations disclosed herein. Also contemplated is a sanitary napkin 20 with adhesive layer 90 and microcapsules only on the flaps 54. Another embodiment is a sanitary napkin 20 having frangible microcapsules 96 connected to the release liner 56 which burst upon the removal of the release liner 56 from the adhesive layer 90 of the sanitary napkin 20, thus releasing perfume.

Another embodiment is contemplated wherein diffusion microcapsules 95 begin to release perfume during the course of the wear of the sanitary napkin 20, wherein this diffusion either terminates at removal of the napkin 20 from the wearer's undergarment or continues to diffuse perfume after the wear and disposal of the napkin 20, thus providing continued post-wear protection from body malodor.

Another alternative embodiment herein comprises an attachment system which uses mechanical fastening means, e.g. hook and loop, or a combination of mechanical fastening means and adhesive means. In this embodiment, microcapsules could be embedded within the hooks and/or loop portions of the attachment system. A mechanical attachment system substantially using hooks with microcapsules embedded therein and which attaches directly to wearer's undergarment is preferred. Also preferred is an attachment system comprising a combination hook and adhesive attachment means with microcapsules embedded therein.

Exemplary attachment systems comprising hook and loop fastening materials is disclosed in U.S. Pat. No. 4,869,724 issued to Scripps on Sep. 26, 1989. Attachment systems utilizing mechanical closure elements are also disclosed in U.S. Pat. No. 4,846,815 issued to Scripps on Jul. 11, 1989; and U.S. Pat. No. 4,894,060 issued to Nestegard on Jan. 16, 1990. Attachment systems having combination adhesive/mechanical closure elements are described in U.S. Pat. No. 4,946,527 issued to Battrell on Aug. 7, 1990. Each of these patents are incorporated herein by reference.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sanitary napkin for placement in a wearer's undergarment, said sanitary napkin having a longitudinal axis, a lateral axis, longitudinal edges, end edges, and a central portion, said sanitary napkin comprising:

a liquid pervious topsheet;

a liquid impervious backsheet joined to said topsheet, said backsheet having and outer surface and an inner surface;

an absorbent core positioned between said topsheet and said backsheet;

an attachment system secured to said outer surface of said backsheet for securing said sanitary napkin to a wearer's undergarment, said attachment system comprising an adhesive layer having a release liner thereon to protect said adhesive layer prior to engagement of said sanitary napkin with a wearer's undergarment; and a plurality of perfume-filled microcapsules being at least partially embedded within said attachment system, said microcapsules diffusely releasing perfume at a steady-state throughout the engagement of said sanitary napkin with a user's undergarment.

2. The sanitary napkin of claim 1 wherein said microcapsules provide a fragrance burst upon removal of said release liner from said adhesive layer.

3. The sanitary napkin of claim 1 wherein said microcapsules provide a fragrance burst upon disengagement of said sanitary napkin from a wearer's undergarments.

4. The sanitary napkin of claim 1 wherein said microcapsules provide a fragrance burst upon removal of said release liner from said adhesive layer and provide a fragrance burst upon disengagement of said sanitary napkin from a wearer's undergarments.

5. The sanitary napkin of claim 1 comprising a pair of flaps having a garment side and an attachment system positioned on said garment side for attachment of said sanitary napkin to a wearer's undergarment, each said flap being associated with said central portion at a juncture and extending laterally outward beyond a longitudinal edge of said central portion, each said juncture having a pair of ends, said flaps being divided into a front half and a back half by a flap transverse centerline.

6. The sanitary napkin of claim 5 wherein said attachment system on said flaps comprises an adhesive layer having release liner thereon to protect said adhesive layer prior to engagement of said sanitary napkin with a wearer's undergarment.

7. The sanitary napkin of claim 6 wherein said adhesive layer on said flaps comprises perfume-filled microcapsules, said microcapsules diffusely releasing perfume at a steady-state throughout the engagement of said sanitary napkin with a user's undergarment.

8. The sanitary napkin of claim 7 wherein said microcapsules on said flaps provide a fragrance burst upon disengagement of said sanitary napkin from a wearer's undergarment.

9. The sanitary napkin of claim 7 wherein said microcapsules on said flaps provide a fragrance burst upon removal of said release liner from said adhesive layer.

10. A sanitary napkin for placement in a wearer's undergarment, said sanitary napkin having a longitudinal axis, a lateral axis, longitudinal edges, end edges, and a central portion, said sanitary napkin comprising:

a liquid pervious topsheet;

a liquid impervious backsheet joined to said topsheet, said backsheet having an outer surface and an inner surface;

an absorbent core positioned between said topsheet and said backsheet;

a pair of flaps having a garment side and an attachment system on said garment side for attachment of said sanitary napkin to a wearer's undergarment, each said flap being associated with said central portion at a juncture and extending laterally outward beyond a longitudinal edge of said central portion, each said juncture having a pair of ends, said flaps being divided into a front half and a back half by a flap transverse centerline; and a plurality of perfume-filled microcapsules at least partially embedded within said attachment system, said microcapsules diffusely releasing perfume at a steady-state throughout the engagement of said sanitary napkin with a user's undergarment.

11. The sanitary of claim 10 wherein said attachment system comprises an adhesive layer having a release liner thereon to protect said adhesive layer prior to engagement of said sanitary napkin with a wearer's undergarment.

12. The sanitary of claim 10 wherein said adhesive layer comprises perfume-filled microcapsules providing a fragrance burst upon removal of said release liner from said adhesive layer.

13. The sanitary of claim 10 wherein said adhesive layer comprise perfume-filled microcapsules, said microcapsules diffusely releasing perfume at a steady-state throughout the engagement of said sanitary napkin with a user's undergarment upon removal of said release liner.

14. The sanitary napkin of claim 10 wherein said adhesive layer comprises perfume-filled microcapsules, said microcapsules providing a fragrance burst upon disengagement of said sanitary napkin from a wearer's undergarment.

15. The sanitary napkin of claim 10 wherein said attachment system comprises hooks and loops.

16. A sanitary napkin for placement in a wearer's undergarment, said sanitary napkin having a longitudinal axis, a lateral axis, longitudinal edges, end edges, and a central portion, said sanitary napkin comprising:

a liquid pervious topsheet;

a liquid impervious backsheet joined to said topsheet, said backsheet having an outer surface and an inner surface;

an absorbent core positioned between said topsheet and said backsheet;

an attachment system secured to said outer surface of said backsheet for securing said sanitary napkin to a wearer's undergarment, said attachment system comprising an adhesive layer having a release liner thereon to protect said adhesive layer prior to engagement of said sanitary napkin with a wearer's undergarment; and a plurality of perfume-filled microcapsules being at least partially embedded within said attachment system, at least one of said microcapsules diffusely releasing perfume at a steady-state throughout the engagement of said sanitary napkin with a user's undergarment, at least one of said microcapsules providing a fragrance burst upon removal of said release liner from said adhesive layer, and at least one of said microcapsules providing a fragrance burst upon disengagement of said sanitary napkin from a user's undergarment.

* * * * *

UNITED STATES PATENT AND TRADEMARK OFFICE
CERTIFICATE OF CORRECTION

PATENT NO. : 5,591,146
DATED : January 7, 1997
INVENTOR(S) : MARGARET H. HASSE

It is certified that error appears in the above-identified patent and that said Letters Patent is hereby corrected as shown below:

*Column 4, line 33, "fight" should read --right--.*

*Column 5, line 8, "foams:" should read –foams;--.*

*Column 6, line 51, "at." should read –al.--.*

*Column 9, line 43, "iso-bomyl" should read –iso-bornyl--.*

*Column 10, line 2, "gamma-metyhyl" should read –gamma-methyl--.*

*Column 12, line 6, "carded" should read --carried--.*

*Column 12, line 55, "microcapsule-beating" should read –microcapsule-bearing--.*

*Column 13, line 45, "Sagatin" should read --Sagarin--.*

*Column 14, line 58, "and" should read --an--.*

*Column 16, line 20, "comprise" should read --comprises--.*

Signed and Sealed this

Seventh Day of September, 1999

Attest:

Q. TODD DICKINSON

*Attesting Officer*   Acting Commissioner of Patents and Trademarks